US00PP36621P2

(12) United States Plant Patent
Cameron et al.

(10) Patent No.: US PP36,621 P2
(45) Date of Patent: Apr. 22, 2025

(54) ***GAZANIA* PLANT NAMED 'GAZ1901A'**

(50) Latin Name: ***Gazania tomentosa* X *Gazania rigens***
Varietal Denomination: GAZ1901A

(71) Applicants: Andrew Cameron, Arcadia (AU); Sonja Cameron, Arcadia (AU)

(72) Inventors: Andrew Cameron, Arcadia (AU); Sonja Cameron, Arcadia (AU)

( * ) Notice: Subject to any disclaimer, the term of this patent is extended or adjusted under 35 U.S.C. 154(b) by 0 days.

(21) Appl. No.: 18/738,929

(22) Filed: Jun. 10, 2024

(51) Int. Cl.
*A01H 6/14* (2018.01)
*A01H 5/02* (2018.01)

(52) U.S. Cl.
USPC ..... Plt./334

(58) Field of Classification Search
USPC ..... Plt./263.1, 334
See application file for complete search history.

(56) References Cited

U.S. PATENT DOCUMENTS

PP18,418 P2 * 1/2008 Bolwell ..... A01H 5/02
Plt./334

* cited by examiner

*Primary Examiner* — Karen M Redden
(74) *Attorney, Agent, or Firm* — C. Anne Whealy

(57) ABSTRACT

A new and distinct cultivar of *Gazania* plant named 'GAZ1901A', characterized by its compact, semi-upright to outwardly spreading, low-growing and flat to slightly mounded plant habit; vigorous growth habit; freely branching habit; densely pubescent silvery green-colored leaves; freely flowering habit; long flowering period; daisy-type inflorescences with white-colored ray florets that are proximally blushed with yellow and darker yellow-colored disc florets; and good garden performance.

3 Drawing Sheets

Figure 1:
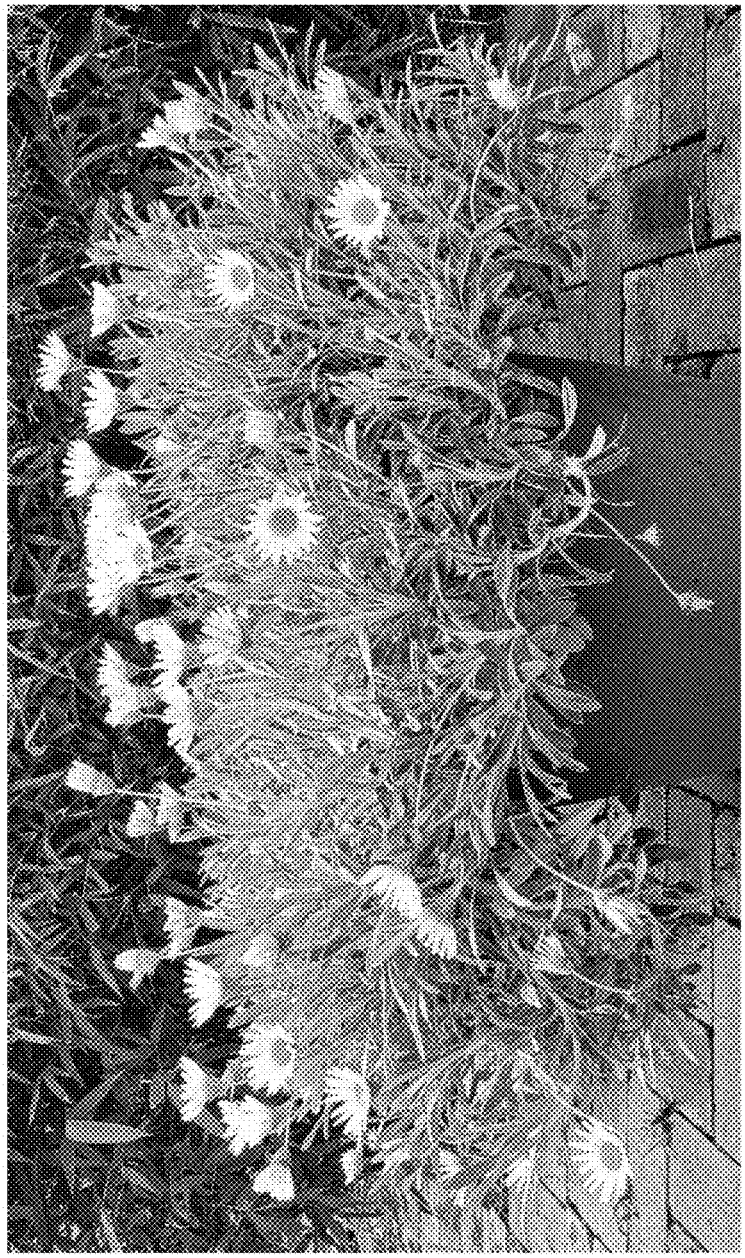

Botanical designation: *Gazania tomentosa* X *Gazania rigens*.

Cultivar denomination: 'GAZ1901A'.

BACKGROUND OF THE INVENTION

The present invention relates to a new and distinct cultivar of *Gazania* plant, botanically known as *Gazania tomentosa* X *Gazania rigens* and hereinafter referred to by the name 'GAZ1901A'. *Gazania* plants are native to Southern Africa and have daisy-type composite inflorescences. *Gazania* plants are nyctinastic, that is, inflorescences will open during the day in high light conditions and will close at night or under low light conditions. The new *Gazania* plant, 'GAZ1901A', is the result of a breeding program with the objective of producing new and unique *Gazania* plants with silvery green-colored foliage and attractive inflorescences with whitish-colored ray florets.

The new *Gazania* plant originated from a cross-pollination conducted by the Inventors in Arcadia, New South Wales, Australia in 2019, of an unnamed selection of *Gazania tomentosa*, not patented, as the female, or seed, parent with an unnamed selection of *Gazania rigens*, not patented, as the male, or pollen, parent. The new *Gazania* plant was discovered and selected by the Inventors as a single flowering plant within the progeny of the stated cross-pollination in a controlled environment in Arcadia, New South Wales, Australia in September, 2019.

Asexual reproduction of the new *Gazania* plant by vegetative terminal cuttings in a controlled greenhouse environment in Arcadia, New South Wales, Australia since December, 2019, has shown that the unique features of this new *Gazania* plant are stable and reproduced true to type in successive generations.

SUMMARY OF THE INVENTION

Plants of the new *Gazania* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of the new *Gazania* plant. These characteristics in combination distinguish 'GAZ1901A' as a new and distinct cultivar of *Gazania:*

1. Compact, semi-upright to outwardly spreading, low-growing and flat to slightly mounded plant habit.
2. Vigorous growth habit.
3. Freely branching habit.
4. Densely pubescent silvery green-colored leaves.
5. Freely flowering habit.
6. Long flowering period.
7. Daisy-type inflorescences with white-colored ray florets that are proximally blushed with yellow and darker yellow-colored disc florets.
8. Good garden performance.

Plants of the new *Gazania* differ from plants of the female parent selection primarily in ray floret color as ray florets of plants of the new *Gazania* are white in color and proximally blushed with yellow whereas ray florets of plants of the female parent selection are yellow in color.

Plants of the new *Gazania* differ from plants of the male parent selection primarily in leaf texture and color as leaves of plants of the new *Gazania* are densely pubescent and silvery green in color whereas leaves of plants of the male parent selection are slightly pubescent and medium green in color.

Plants of the new *Gazania* can be compared to plants of the *Gazania rigens* 'New Day', not patented. In side-by-side comparisons, plants of the new *Gazania* differed primarily from plants of 'New Day' in the following characteristics:

1. Leaves of plants of the new *Gazania* are densely pubescent and silvery green in color whereas leaves of plants of 'New Day' are slightly pubescent and medium green in color.
2. Ray florets of plants of the new *Gazania* are white in color and proximally blushed with yellow whereas ray florets of plants of 'New Day' are white in color and proximally, brownish red.

BRIEF DESCRIPTION OF THE PHOTOGRAPHS

The accompanying photographs illustrate the overall appearance of the new *Gazania* plant and show the colors as true as it is reasonably possible to obtain in colored reproductions of this type. Colors in the photographs may differ slightly from the color values cited in the detailed botanical description which accurately describe the colors of the new *Gazania* plant.

The photograph on the first sheet (FIG. 1) is a side perspective view of a typical flowering plant of 'GAZ1901A' grown in a container.

Figure 2:
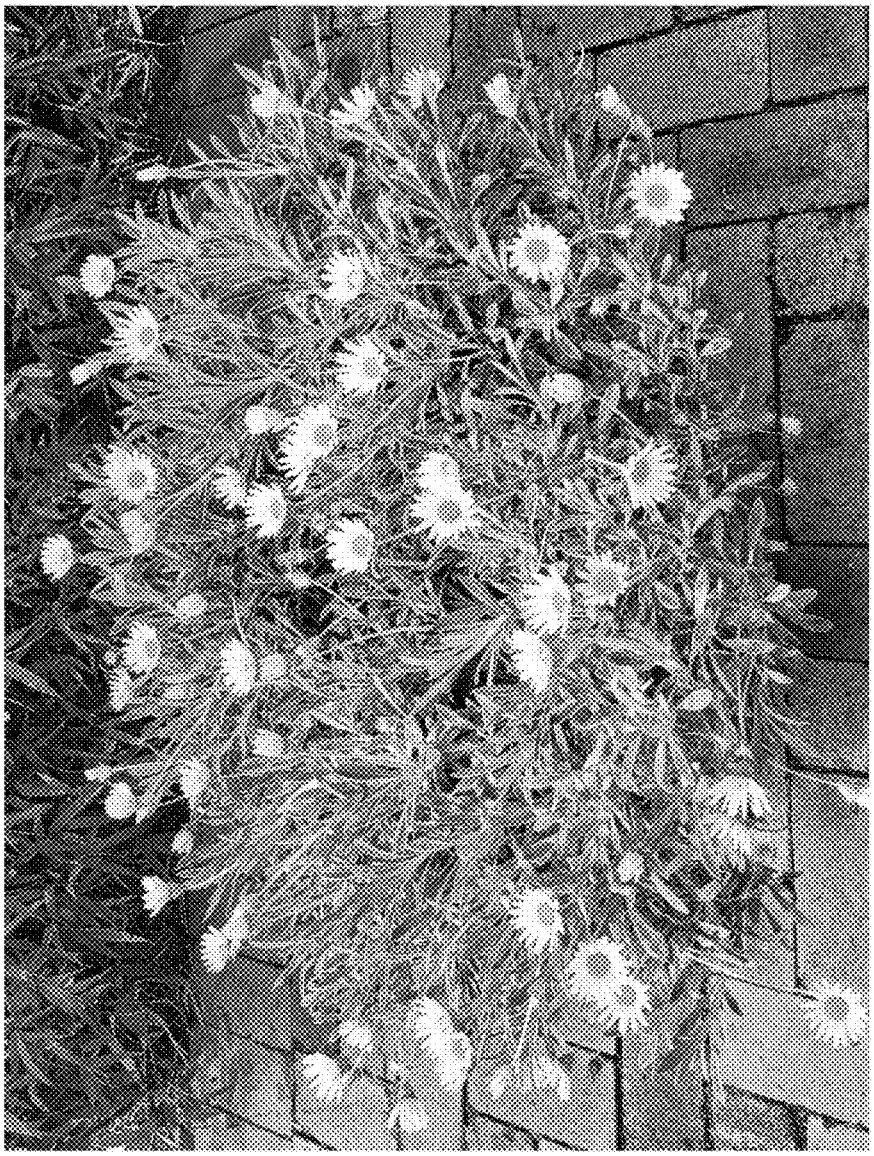

The photograph on the second sheet (FIG. 2) is a top perspective view of a typical flowering plant of 'GAZ1901A' grown in a container.

Figure 3:
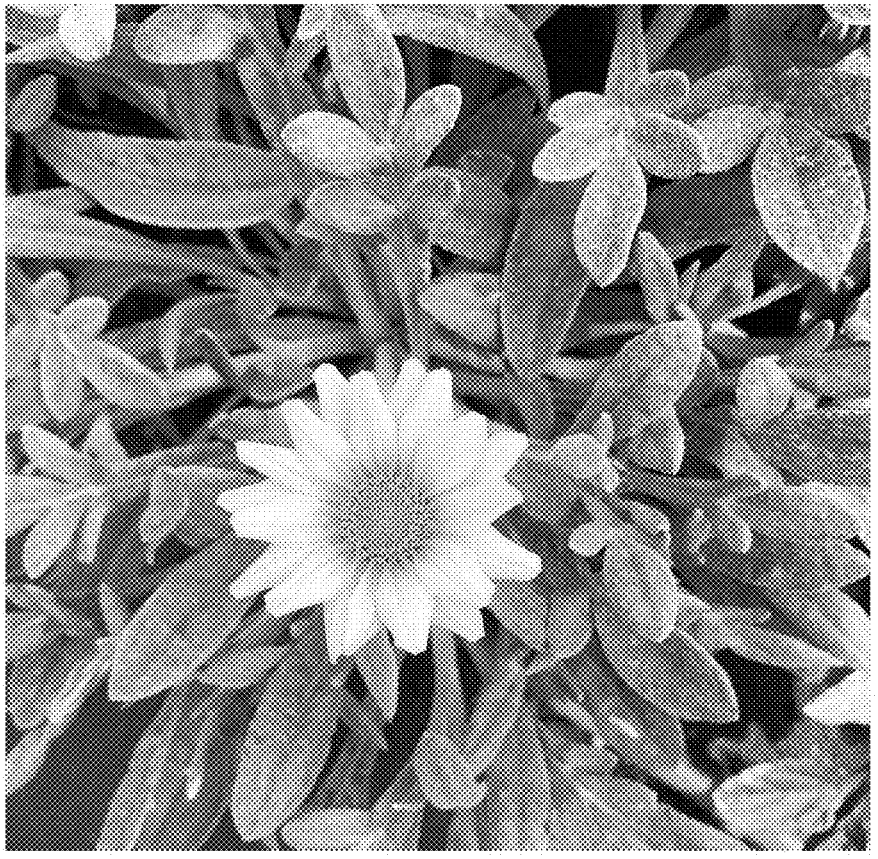

The photograph on the third sheet (FIG. 3) is a close-up view of a typical flowering plant of 'GAZ1901A'.

Plants used for the photographs were grown in 40-cm containers in an outdoor nursery in Arcadia, New South Wales, Australia and were 18 months old when the photographs were taken.

DETAILED BOTANICAL DESCRIPTION

Plants used for the following observations and measurements were grown during the late summer to early autumn in Arcadia, New South Wales, Australia and under conditions and cultural practices which approximate those generally used in commercial container *Gazania* production. Plants were grown in 20-cm containers in an outdoor nursery and were four months from planting when the description was taken. During the production of the plants, day temperatures ranged from 20° C. to 35° C., night temperatures ranged from 13° C. to 20° C. and light levels ranged from 5 to 10,000 foot-candles. In the following description, color references are made to The Royal Horticultural Society Colour Chart, 2015 Edition, except where general terms of ordinary dictionary significance are used.

Botanical classification: *Gazania tomentosa* X *Gazania rigens* 'GAZ1901A'.

Parentage:

*Female, or seed, parent*.—Unnamed selection of *Gazania tomentosa*, not patented.

*Male, or pollen, parent*.—Unnamed of *Gazania rigens*, not patented.

Propagation:

*Type*.—By vegetative terminal cuttings.

*Time to initiate roots, summer*.—About two weeks at temperatures of about 22° C. to 32° C.

*Time to initiate roots, winter*.—About three weeks at temperatures of about 12° C. to 20° C.

*Time to produce a rooted young plant, summer*.—About five to six weeks at temperatures of about 22° C. to 32° C.

*Time to produce a rooted young plant, winter*.—About seven to eight weeks at temperatures of about 12° C. to 20° C.

*Root description*.—Fibrous, fine in thickness; typically white in color; actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, semi-upright to outwardly spreading, low-growing and flat to slightly mounded plant habit; vigorous growth habit; strong and freely branching habit with about ten primary lateral branches per plant; with subsequent development, plant habit will become cascading.

*Plant height*.—About 20 cm.

*Plant width*.—About 40 cm.

*Lateral branches*.—Length: About 15 cm. Internode length: About 1 cm. Strength: Strong. Texture: Pubescent. Color: Close to 196D.

Leaf description:

*Arrangement*.—Irregularly whorled; simple.

*Length*.—About 9 cm to 10 cm.

*Width*.—About 15 cm to 22 cm.

*Shape*.—Typically, not lobed and oblanceolate in overall shape; if lobed, pinnatisect with two to five lobes.

*Apex*.—Acute.

*Base*.—Attenuate, decurrent.

*Margin*.—Entire.

*Texture and luster, upper surface*.—Densely pubescent, flocculent; matte.

*Texture and luster, lower surface*.—Densely pubescent; matte.

*Venation pattern*.—Pinnate and reticulate.

*Color*.—Developing leaves, upper surface: Close to NN155D; without pubescence, close to 147A. Developing leaves, lower surface: Close to NN155D. Fully expanded leaves, upper surface: Close to N189B to N189C; with pubescence, close to NN137A with venation, close to NN137B. Fully expanded leaves, lower surface: Close to NN155D.

*Petiole length*.—About 2.2 cm.

*Petiole texture, upper and lower surfaces*.—Densely pubescent; matte.

*Petiole color, upper and lower surfaces*.—Close to NN155D.

Inflorescence description:

*Appearance*.—Daisy type inflorescence form with ligulate-shaped ray florets; inflorescences borne on terminals and held above the foliar plane; disc and ray florets arranged acropetally on a capitulum; inflorescences not fragrant.

*Flowering season*.—Long flowering period; plants flower from spring to early fall in New South Wales, Australia; flowering continuous during this period.

*Quantity of inflorescences*.—About 20 inflorescences per plant at one time.

*Inflorescence buds*.—Height: About 1.8 cm. Diameter: About 1.5 cm. Shape: Ovoid; distally, conical. Texture and luster: Densely pubescent; matte. Color: Close to NN155D; with pubescence removed, close to 144A.

*Inflorescence size*.—Diameter: About 5 cm. Depth (height): About 3.5 cm. Diameter of disc: About 1.3 cm. Receptacle height: About 1.2 cm. Receptacle diameter: About 1 cm.

*Ray florets*.—Orientation and arrangement: Initially upright, then about 30° from vertical, eventually close to perpendicular to the peduncle; not reflexing; about 21 ray florets in a single whorl; ray florets imbricate. Length: About 1.8 cm to 2.3 cm. Width: About 8 mm to 9 mm. Shape: Ligulate. Apex: Abruptly acute. Base: Fused into short tube. Margin: Entire. Texture and luster, upper and lower surfaces: Smooth, glabrous; satiny; matte. Color: When opening, upper surface: Close to NN155C to NN155D. When opening, lower surface: Close to NN155A; fine longitudinal stripes, close to 189B. Fully opened, upper surface: Close to between NN155C to NN155D and 157B; proximally, close to 12B. Fully opened, lower surface: Close to between 155A to 1D; proximally, close to 12B to 12C; fine longitudinal stripes, close to 189B.

*Disc florets*.—Arrangement: Massed at center of receptacle. Length: About 1 cm. Width: Distally, about 1.5 mm and proximally, about 1 mm. Shape: Tubular, elongated, enlarged. Apex: Five-pointed. Number of disc florets per inflorescence: About 120. Color, mature: Close to 2A.

*Phyllaries*.—Number of phyllaries per inflorescence: About 36 arranged in two to three whorls. Length: About 7 mm to 9 mm. Width: About 2 mm to 3 mm. Shape: Deltoid. Apex: Acute. Base: Fused. Margin: Entire. Texture, upper surface: Slightly pubescent. Texture, lower surface: Moderately pubescent. Color, upper surface: Close to 151B; proximally, close to 146A. Color, lower surface: Close to N189B to N189C.

*Peduncles*.—Length: About 14 cm to 19 cm. Diameter: About 3 mm. Angle: Mostly upright to outwardly leaning. Strength: Strong. Texture: Pubescent, flocculent. Color: Close to between 145C and 194D.

*Reproductive organs*.—Androecium: Stamens per floret: About five. Pollen color: Close to 15A to 15B. Gynoecium: Only observed on disc florets. Pistil length: About 1 cm. Stigma shape: Two-parted. Stigma color: Close to 2AB. Ovary color: Close to 155A.

*Seeds and fruit*.—To date, seed and fruit production has not been observed on plants of the new *Gazania*.

Pathogen and pest resistance: To date, resistance to pathogens and pests common to *Gazania* plants has not been observed on plants of the new *Gazania* grown under commercial conditions.

Garden performance: Plants of the new *Gazania* have been observed to have good garden performance and to tolerate various light levels, wind, rain, neglect and temperatures from about 5° C. to about 42° C.

It is claimed:

1. A new and distinct *Gazania* plant named 'GAZ1901A' as herein illustrated and described.

* * * * *